United States Patent [19]

Becker et al.

[11] Patent Number: 4,835,003
[45] Date of Patent: May 30, 1989

[54] MEDICAL TUBING WITH WATER-ACTIVATED LUBRICATING COATING

[75] Inventors: Lawrence F. Becker, Fox Lake; Dean G. Laurin, Lake Zurich; Joseph A. Palomo, Round Lake, all of Ill.

[73] Assignee: Baxter International Inc., Deerfield, Ill.

[21] Appl. No.: 724,223

[22] Filed: Apr. 17, 1985

[51] Int. Cl.[4] .......................... B32B 1/08; B32B 1/10; B32B 25/08; B32B 27/08
[52] U.S. Cl. ........................................ 427/2; 427/336; 427/353; 427/393.5; 428/36.91; 428/423.1; 428/423.3; 428/424.2; 523/105; 525/123
[58] Field of Search ............... 428/423.3, 423.7, 424.2, 428/36, 423.1; 525/123; 523/105, 112; 427/2, 393.5, 336, 353; 604/749

[56] References Cited

U.S. PATENT DOCUMENTS

| | | | |
|---|---|---|---|
| 4,100,309 | 7/1978 | Michlus et al. | 428/423.3 |
| 4,119,094 | 10/1978 | Micklos et al. | 428/423.3 |
| 4,277,576 | 7/1981 | Straub et al. | 525/123 |
| 4,666,437 | 5/1987 | Lambert | 428/423.7 |

*Primary Examiner*—Allan M. Lieberman
*Attorney, Agent, or Firm*—Charles R. Mattenson; Robert R. Barrett; Paul C. Flattery

[57] ABSTRACT

Medical tubing carries on at least a portion of its length a water-activated lubricating coating of a hydrophilic thermoplastic resin which is adhesively compatible with the material of the medical tubing and polyvinyl pyrrolidone having a molecular weight of at least 200,000, in the form of a dispersed separate phase in the thermoplastic resin upon hydration. The polyvinyl pyrrolidone provides long-lasting lubrication when wet.

5 Claims, 1 Drawing Sheet

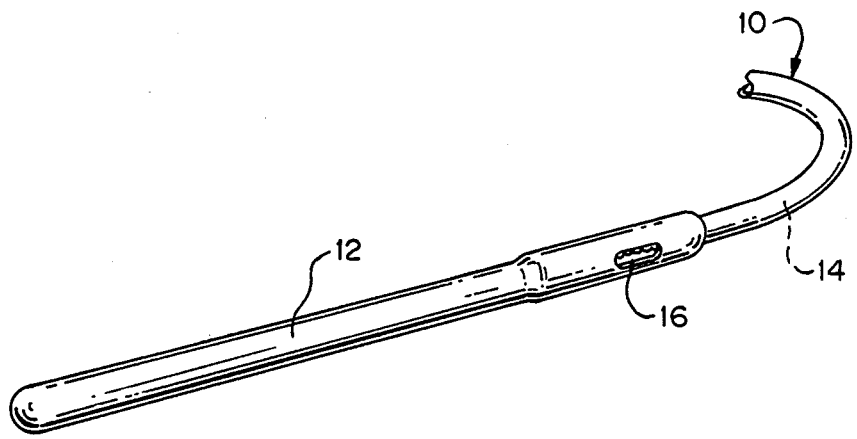

MEDICAL TUBING WITH WATER-ACTIVATED LUBRICATING COATING

TECHNICAL FIELD

There is a need in the field of medical tubing to provide a slippery surface so that the tubing can be easily installed into a body or the like. This has been done by placing mineral oil, for example, in the medical tubing so that it can leach out. Alternatively, mineral oil may be added immediately prior to insertion of the tubing.

In Micklus U.S. Pat. Nos. 4,100,309 and 4,119,094, a polyvinyl pyrrolidone-polyurethane interpolymer is used on flexible articles to provide lubrication upon wetting.

In accordance with this invention, a simplified, effective system provides lubrication on wetting to flexible articles, particularly materials made of rubber or flexible thermoplastic resin. The water-activated lubricating coating contains free, separable polyvinyl pyrrolidone, not chemically bonded to any substrate and not part of an interpolymer.

DESCRIPTION OF THE INVENTION

By this invention, a flexible article such as medical tubing made of a resin such as a cured rubber or a thermoplastic material may carry on at least a portion of its length a water-activatable lubricating coating.

In accordance with this invention, the coating may comprise 1.5 to 10 parts by weight of a hydrophilic resin which is adhesively compatible with the material of said medical tubing and adheres thereto, and from 0.1 to 15 parts by weight of a water soluble polymer having a molecular weight of at least 200,000 and defining, upon hydration, a dispersed, separate phase in the resin coating, so that hydration causes the water soluble polymer to form a lubricating film on the article.

The coating may be applied to the medical tubing using a volatile solvent vehicle, in solution or as an emulsion with the volatile solvent. The two ingredients, typically a hydrophilic polyurethane resin and polyvinyl pyrrolidone, should be intimately mixed, so that as the volatile solvent dries, leaving behind the coating, the polyvinyl pyrrolidone forms a separate phase from the resin, intimately dispersed throughout the polyurethane coating. Accordingly, the polyvinyl pyrrolidone bleeds to the surface to provide a lubricating characteristic.

It is particularly preferred for the resin used in the coating to be hydrophilic in nature, but of a character so that it is basically incompatible with the polyvinyl pyrrolidone (PVP) so that the PVP forms a separate phase within the coating. When such a resin is used, upon addition of water, the water can rapidly diffuse into the hydrophilic coating, displacing PVP and causing a continuous flow of PVP to the surface, for a continued, long-lasting, slippery characteristic while the surface is wet. As a further advantage, when such a hydrophilic resin is used in the coating, the polyvinyl pyrrolidone can form a dispersed, separate phase which is in an interconnected, open cell form. This facilitates a long-lasting, slippery lubricating characteristic of the wetted coating of this invention.

One particularly suitable resin for use in the coating of this invention is a hydrophilic polyurethane resin made by the Anderson Development Company of Adrian, Mich. By the term "hydrophilic" it is intended to imply that water droplets do not readily form beads on the surface of such hydrophilic material, but instead the water droplets tend to assume a contact angle of less than 90° with the resin material, and readily form a film on its surface. Also, hydrophilic resins can absorb water and thus swell by typically at least 100 percent of their dry weight.

It is generally preferred for the molecular weight of the polyvinyl pyrrolidone to be at least 800,000, since higher molecular weight material provides improved lubricating characteristics.

Specifically, the coating of this invention may be applied, for example, to polyurethane medical tubing, by forming a mixture of 1.5 to 10 parts by weight of a hydrophilic polyurethane resin solution in 100 parts by weight of a volatile solvent, from 0.1 to 15 or 20 parts by weight of the polyvinyl pyrrolidone having a molecular weight of at least 200,000 or 300,000 and preferably more than 800,000, and 10 to 50 parts by weight of an alcohol having 1 to 3 carbon atoms, preferably ethanol in a concentration of 15 to 25 parts by weight.

The thermoplastic resin which forms the film of this invention is dispersed in a compatible, volatile solvent with the resin being typically in a concentration of about 3 to 10 percent by weight in the solvent. The specific solvent chosen should be compatible enough to provide good dispersion to both the plastic resin and the water soluble polymer so that they can become intimately mixed, for example, in a colloidal solution. Thus the solvent should be compatible for use with both of the polymeric ingredients. Typically when the resin is a polyurethane, tetrahydrofuran may be used, since it is compatible to both polyurethane and PVP. Other solvents may be chosen as may be desired, for example, ethers.

It has been found that the presence of ethanol provides an improved smoothness to the coating, which may be applied by dipping of polyurethane medical tubing, or any other desired article which is adhesively compatible to the hydrophilic polyurethane so that the coating will not fall off.

The cured coating is hazy upon hydration, showing that multiple phases are present, one of the phase being the dispersed, separate PVP phase, or equivalent polymer.

Other candidates for the resin in the coating in this invention may be selected as desired to provide appropriate adhesive properties, while permitting the existence of the separate PVP phase in the coating. Specific examples include poly(ethylene-vinyl alcohol) or block or graft copolymers of nylon or polyester with polyethylene oxide. It is particularly desirable to select resins for the coating which are capable of being intimately dispersable with the PVP in a given solvent system. Also, if desired, preferably water soluble resins for the coating of this invention of higher molecular weight will provide longer lasting lubricating and require even less coating.

Examples of water soluble polymers other than PVP which may be used include high molecular weight (over 200,000) materials such as hyaluronic acid, poly(-hydroxyethyl methacrylate), or gum arabic.

Higher molecular weight polymers can be obtained by adding a polymerization step or by low levels of radiation treatment of the coating either before or after drying, for example, beta or gamma radiation or approximately 0.1 to 5 MRADS. The radiation dosage may be optimized for each system to maximize the lubricating effect while reducing the rate of extraction of the PVP.

Typically, about 3 to 15 parts by weight of PVP are present per 5 parts by weight of hydrophilic polyurethane resin in the coating.

The example below, as well as the preceding disclosure, is provided for illustrative purposes only, and is not intended to limit the scope of the invention of this application, which is as defined in the claims below.

EXAMPLE

A solution of a water soluble polyurethane material is prepared in a 5 weight percent concentration in 100 ml. of tetrahydrofuran (5 gms. of polyurethane). The polyurethane material is manufactured by the Anderson Development Company of Adrian, Mich., and is a film forming polymer of the reaction product of hexamethylene diisocyanate reacted with polytetramethylene glycol 1,000 to form a prepolymer having isocyanate end blocks. The prepolymer is further extended with another polyether (Wyandotte Pluracol F 108) and then stepwise extended with polyethylene glycol of 7,000 molecular weight, 1,4-butane diol and ethylene diamine.

Following this, 7.2 grams of polyvinyl pyrrolidone having a molecular weight on the order of one million was added (povidone USP K-90, sold by GAF). The solution is sufficiently agitated to thoroughly disperse the polyvinyl pyrrolidone.

One then adds 20 ml. (16.8 gms.) of ethyl alcohol. The resulting clear solution is placed on a roller mill for five minutes, taken off the mill, and allowed to settle for five minutes to remove bubbles from the mixture.

An enteral feed tube made by Travenol Laboratories, Inc. and formulated by Thermo Electrons's Tecoflex polyurethane 80A and containing 20 percent barium sulfate is used as the catheter to be coated in this example.

Referring to the drawing, a perspective view of the enteral feed tube is disclosed.

As shown in the drawing, the enteral feed tube 10 has a bolus section 12 which carries weight material, for example tungsten beads. Feed tube 10 defines a hollow bore 14 along its length, terminating in bolus 12 which may be solid. Inlet ports 16 are defined adjacent the bolus.

A stylet which may be used in the feed tube for insertion is removed. Using a container filled with the coating solution made as described above, bolus 12 is dipped to just below ports 16, and held in the solution for five seconds. The tube is then removed quickly from the solution, making sure that it does not touch the sides of the container in which the solution is held. A drop of solution may form at the bottom of the bolus, which drop may be removed. The bolus is allowed to air dry.

The coating will dry completely in 30 minutes at about 75° F. It is not strongly slippery when dry, but will be slippery within five seconds after immersion in water, and will maintain its lubricity for at least about one hour while immersed in water. Accordingly, this slippery front end of an enteral feeding tube can greatly facilitate the insertion of the tube through the esophagus into the stomach or bowels of a patient.

That which is claimed is:

1. The method of coating at least a portion of medical tubing with a mixture which comprises 1.5 to 10 parts by weight of a hydrophilic polyurethane resin solution in 100 parts by weight of a volatile solvent containing 1.5 to 10 weight percent of said resin, from 0.1 to 20 parts by weight of polyvinyl pyrrolidone having a molecular weight of at least 200,000, and 10 to 50 parts by weight of an alcohol having 1 to 3 carbon atoms; and thereafter allowing the coated medical tubing to dry, whereby a water-activated lubricating coating is provided to said medical tubing.

2. The method of claim 1 in which from 5 to 10 parts of said polyvinyl pyrrolidone is present.

3. The method of claim 2 in which said polyvinyl pyrrolidone has a molecular weight of at least 800,000.

4. The method of claim 3 in which said alcohol is ethyl alcohol.

5. The method of claim 4 in which from 15 to 25 parts by weight of said ethyl alcohol are present.

* * * * *